US005747259A

United States Patent [19]

You

[11] Patent Number: 5,747,259
[45] Date of Patent: May 5, 1998

[54] MATERIALS AND METHODS FOR SPECIES-SPECIFIC DETECTION OF MYCOBACTERIUM KANSASII NUCLEIC ACIDS

[75] Inventor: Qimin You, Cockeysville, Md.

[73] Assignee: Becton, Dickinson and Company, Franklin Lakes, N.J.

[21] Appl. No.: 682,218

[22] Filed: Jul. 17, 1996

[51] Int. Cl.[6] ............... C12Q 1/68; C12P 19/34; C07H 21/04
[52] U.S. Cl. ............... 435/6; 435/91.1; 435/91.2; 536/24.3; 536/24.32
[58] Field of Search ............... 536/24.3, 24.32; 435/6, 91.2, 91.1

[56] References Cited

U.S. PATENT DOCUMENTS

| | | | |
|---|---|---|---|
| 5,436,155 | 7/1995 | Bell | 435/252.3 |
| 5,500,341 | 3/1996 | Spears | 435/6 |

OTHER PUBLICATIONS

Aoki et al. Complete amino acid sequence of the large subunit of the low–Ca2+–requiring form of human Ca2+–activated neutral protease (uCANP) deduced from its cDNA sequence, FEBS LETTERS, vol. 205, No. 2, pp. 313–317, 1986.

T. Rogall, et al. "Differentiation of Mycobacterium species by direct sequencing of amplified DNA" *J. Gen. Microbiol.* 136:1915–1920 (1990).

E. Tortoli, et al. "Evaluation of a Commercial DNA Probe Assay for the Identification of Mycobacterium kansasii" *Eur. J. Clin. Microbiol. Infect. Dis.* 13:264–267 (1994).

B. C. Ross, et al. "Identification of a Genetically Distinct Subspecies of Mycobacterium kansasii" *J. Clin. Microbiol.* 30:2930–2933 (1992).

Z. H. Huang, et al. "Identification of Mycobacterium kansasii by DNA Hybridization" *J. Clin. Microbiol.* 29:2125–2129 (1991).

J. Welsh and M. McClelland "Fingerprinting genomes using PCR with arbitrary primers" *Nucl. Acids Res.* 18:7213–7218 (1980).

M. Yang, et al. "Isolation of a DNA Probe for Identification of Mycobacterium kansasii, Including the Genetic Subgroup" *J. Clin. Microbiol.* 31:2769–2772 (1993).

B. Boddinghaus, et al. "Detection and Identification of Mycobacteria and Amplification of rRNA" *J. Clin. Microbiol.* 28:1751–1759 (1990).

*Primary Examiner*—Kenneth R. Horlick
*Assistant Examiner*—Joyce Tung
*Attorney, Agent, or Firm*—Donna R. Fugit

[57] ABSTRACT

A newly-identified *M. kansasii* DNA sequence is described and designated KATS1. This sequence is highly *M. kansasii*-specific in nucleic acid hybridization assays and is useful for detecting both typical and atypical strains. KATS1 and segments of the KATS1 sequence are useful for species detection of *M. kansasii* in hybridization or nucleic acid amplification assays with 100% specificity and no cross-reactivity to non-*M. kansasii* species.

16 Claims, No Drawings

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CGTCATGCTG AAGTCCCT                                                        18
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
TCTGTCTCCT GGCACTCT                                                        18
```

( 2 ) INFORMATION FOR SEQ ID NO:3:

( i ) SEQUENCE CHARACTERISTICS:
        ( A ) LENGTH: 656 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: LCDC724

( x i ) SEQUENCE DESCRIPTION: SEQ ID NO:3:

```
GGTCGCGTAA CTCGGTGCCG ATGAGGTCGC CGTATTCGTA GGCGATTTCG GGATCCCAGC          60
TCGAGGCCTC GGCCACACCG GAAGGCAGCG CCGTGGAATA GCGGCTACGC GGTGCTCCAC         120
GGGCAACACC AACGGCGGCA TCGGACATCT GCAGGTCGGG AATCCCCAAG CGTTCAATAC         180
CGGGAATAAA ACCCGCGCCC CCAAGAGAAC GCACGCCAGG CACTGACGTG GCTCCCTCAA         240
GGAGAGTCCG CCATCCCAAG CCGTGAAGCA ATTGCACTTT TCGTCGAGC GTCATCTGCT          300
GGATGACCAG ATCGGCCCGC TCATCAGGAG AGAGGTATTT GTTTCCCAT GGGCGTTCGG          360
GTGCGGCATT TACCGGTTGT CTGAATTGCG TGTACATTGG GGCCGAGGCG ACAAGAAAGA         420
AGAATGCCAG TATTAAATTA GCTGCTTTCA GCAGGGACCT GCGCAGAATC ATCGATTGCG         480
CTCCAGAAAT CTCGTCAGAT CGATCAGCTC CTCCGTTTCG GTTTGACTT CCTGGGAAAT          540
CATCGACCAT CGCGGCCGGC CGAACCAGAT CACGTGCTCC GAGCTTGCGC TCGTAGGCAA         600
TGAGGTTCGG CTTCGCCCGG TCTCCAGTAA AGAGCCTTTG ACCCTGATGC GTTTCC             656
```

( 2 ) INFORMATION FOR SEQ ID NO:4:

( i ) SEQUENCE CHARACTERISTICS:
        ( A ) LENGTH: 655 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
    ( B ) STRAIN: TMC1201

( x i ) SEQUENCE DESCRIPTION: SEQ ID NO:4:

| | | | | | |
|---|---|---|---|---|---|
| GGTCGCGAAG | CTCGGTGCCG | ATGAGGTTGC | CGTATTCGTA | TGCGATTTCT | GGATCCCAGC | 60 |
| TCGAGGCTTC | AGCCACGCCG | GAAGGCAGCG | CCGTGGAATA | GCGGCTACGC | GGGGCTCCAC | 120 |
| GCGCAACACC | AACGGCGGCA | TCGGACATCT | GCAGGTCTGG | AATCCCCAAG | CGCTCGATAC | 180 |
| CGGGGATGAA | ACCCGCGCCC | CCAAGAGGGC | GCACACCAGG | CACTGACGTG | GTTCCCTCAA | 240 |
| GAAGGATCCG | CCATCCCAAG | CCGTGAAGCA | ACTGCACTTT | TTCGTCGAGC | GTCATCTGCT | 300 |
| GGATGACCAG | ATCAGCCCGC | TCATCCGGAG | AGAGATATTT | GTTTCCCAT | GGGCGTATGG | 360 |
| GCCCGGTATT | TATGGGCTGT | CCGAATTGCG | TGTAGATTGG | AGCCGAGGCG | GCAAGAAAGA | 420 |
| GGAACGCCAG | TAGGAGATTC | GCTGCTTTCA | GCAAAGACCT | GCGCATAATC | ATCTATCGTG | 480 |
| CTCCATAAAC | CTCGTCAGAC | CGATCAGCTC | CTATCGTTTC | GGTTTGCTT | CCTTGTGCAC | 540 |
| CATCGACCAT | CGCAACCAGG | CCACCAGATC | ACCCGCTGCG | CGCCTGCGCT | TGTAGGCAAT | 600 |
| GAGGTTCGGC | TTCGCCCGTT | CTCCAGTAAA | GGGCCTTTGG | CCCTGATGCG | TTTCC | 655 |

( 2 ) INFORMATION FOR SEQ ID NO:5:

( i ) SEQUENCE CHARACTERISTICS:
        ( A ) LENGTH: 658 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:5:

| | | | | | |
|---|---|---|---|---|---|
| GGTCGCGWAR | CTCGGTGCCG | ATGAGGTYGC | CGTATTCGTA | KGCGATTTCK | GGATCCCAGC | 60 |
| TCGAGGCYTC | RGCCACRCCG | GAAGGCAGCG | CCGTGGAATA | GCGGCTACGC | GGKGCTCCAC | 120 |
| GSGCAACACC | AACGGCGGCA | TCGGACATCT | GCAGGTCKGG | AATCCCCAAG | CGYTCRATAC | 180 |
| CGGGRATRAA | ACCCGCGCCC | CCAAGAGRRC | GCACRCCAGG | CACTGACGTG | GYTCCCTCAA | 240 |
| GRAGRRTCCG | CCATCCCAAG | CCGTGAAGCA | AYTGCACTTT | TTCGTCGAGC | GTCATCTGCT | 300 |
| GGATGACCAG | ATCRGCCCGC | TCATCMGGAG | AGAGRTATTT | GTTTCCCAT | GGGCGTWYGG | 360 |
| GYSCGGYATT | TAYSGGYTGT | CYGAATTGCG | TGTASATTGG | RGCCGAGGCG | RCAAGAAAGA | 420 |
| RGAAYGCCAG | TAKKARATTM | GCTGCTTTCA | GCARRGACCT | GCGCAKAATC | ATCKATYGYG | 480 |
| CTCCAKAAAY | CTCGTCAGAY | CGATCAGCTC | CTAYCGTTTC | GGTTTGACT | TCCTKGKRMA | 540 |
| YCATCGACCA | TCGCRRCCAG | GCCGAACCAG | ATCACSYGCT | SCGMGCYTGC | GCTYGTAGGC | 600 |
| AATGAGGTTC | GGCTTCGCCC | GKTCTCCAGT | AAAGRGCCTT | TGRCCCTGAT | GCGTTTCC | 658 |

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CGAAGCCGAA CCTCATTG          18

( 2 ) INFORMATION FOR SEQ ID NO:7:

( i ) SEQUENCE CHARACTERISTICS:
        ( A ) LENGTH: 17 base pairs ( B ) TYPE: nucleic acid
( C ) STRANDEDNESS: single
( D ) TOPOLOGY: linear ( x i ) SEQUENCE DESCRIPTION: SEQ ID NO:7:

CTCGGTGCCG ATGAGGT                                                                                    17

( 2 ) INFORMATION FOR SEQ ID NO:8:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:8:

CCGATGAGGT TGCCGTATTC G                                                                               21

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:9:

CAAGAAGGAT CCGCCATCCC                                                                                 20

( 2 ) INFORMATION FOR SEQ ID NO:10:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:10:

ACGCCCATGG GAAAACAAA                                                                                  19

( 2 ) INFORMATION FOR SEQ ID NO:11:

( i ) SEQUENCE CHARACTERISTICS:
( A ) LENGTH: 605 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( B ) STRAIN: LCDC711

( x i ) SEQUENCE DESCRIPTION: SEQ ID NO:11:

| CTCGGTGCCG | ATGAGGTTGC | CGTATTCGTA | TGCGATTTCT | GGATCCCAGC | TCGAGGCTTC | 60 |
| AGCCACGCCG | GAAGGCAGCG | CCGTGGAATA | GCGGCTACGC | GGGGCTCCAC | GCGCAACACC | 120 |
| AACGGCGGCA | TCGGACATCT | GCAGGTCTGG | AATCCCCAAG | CGCTCGATAC | CGGGGATGAA | 180 |
| ACCCGCGCCC | CCAAGAGAGC | GCACACCAGG | CACTGACGTG | GTTCCCTCAA | GAAGGATCCG | 240 |
| CCATCCCAAG | CCGTGAAGCA | ACTGCACTTT | TTCGTCGAGC | GTCATCTGCT | GGATGACCAG | 300 |
| ATCAGCCCGC | TCATCCGGAG | AGAGATATTT | GTTTCCCAT | GGGCGTATGG | GCCCGGTATT | 360 |
| TATGGGCTGT | CCGAATTGCG | TGTAGATTGG | AGCCGAGGCG | GCAAGAAAGA | GGAACGCCAG | 420 |
| TAGGAGATTC | GCTGCTTTCA | GCAAAGACCT | GCGCATAATC | ATCTATCGTG | CTCCATAAAC | 480 |
| CTCGTCAGAC | CGATCAGCTC | CTATCGTTTC | GGTTTTGGCT | TCCTTGTGCA | CCATCGACCA | 540 |

```
TCGCAACCAG GCCACCAGAT CACCCGCTGC GCGCCTGCGC TTGTAGGCAA TGAGGTTCGG      600

CTTCG                                                                  605
```

( 2 ) INFORMATION FOR SEQ ID NO:12:

( i ) SEQUENCE CHARACTERISTICS:
        ( A ) LENGTH: 605 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: LCDC714

( x i ) SEQUENCE DESCRIPTION: SEQ ID NO:12:

```
CTCGGTGCCG ATGTGGTTGC CGTATTCGTA TGCGATTTCT GGATCCCAGC TCGAGGCTTC       60

AGCCCACGCC GGAAGGCAGC GCCGTGGAAT AGCGGCTACG CGGGGCTCCA CGCGCAACAC      120

CAACGGCGGC ATCGGACATC TGCAGGTCTG GAATCCCCAA GCGCTCGATA CCGGGGATGA      180

AACCCGCGCC CCCAAGAGAG CGCACACCAG GCACTGACGT GGTTCCCTCA AGAAGGATCC      240

GCCATCCCAA GCCGTGAAGC AACTGCACTT TTTCGTCGAG CGTCATCTGC TGGATGACCA      300

GATCAGCCCG CTCATCCGGA GAGAGATATT TGTTTCCCA TGGGCGTATG GGCCCGGTAT       360

TTATGGGCTG TCCGAATTGC GTGTAGATTG GAGCCGAGGC GGCAAGAAAG AGGAACGCCA      420

GTAGGAGATT CGCTGCTTTC AGCAAAGACC TGCGCATAAT CATCTATCGT GCTCCATAAA      480

CCTCGTCAGA CCGATCAGCT CCTATCGTTT CGGTTTGCT  TCCTTGTGCA CCATCGACCA      540

TCGCAACCAG GCCACCAGAT CACCCGCTGC GCGCCTGCGC TTGTAGGCAA TGAGGTTCGG      600

CTTCG                                                                  605
```

( 2 ) INFORMATION FOR SEQ ID NO:13:

( i ) SEQUENCE CHARACTERISTICS:
        ( A ) LENGTH: 606 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: T1492

( x i ) SEQUENCE DESCRIPTION: SEQ ID NO:13:

```
CTCGGTGCCG ATGTGGTTGC CGTATTCGTA TGCGATTTCT GGATCCCAGC TCGAGGCTTC       60

AGCCACGCCG GAAGGCAGCC CCCGTGGAAT AGCGGCTACG CGGGGCTCCA CGCGCAACAC      120

CAACGGCGGC ATCGGACATC TGCAGGTCTG GAATCCCCAA GCGCTCGATA CCGGGGATGA      180

AACCCGCGCC CCCAAGAGAG CGCACACCAG GCACTGACGT GGTTCCCTCA AGAAGGATCC      240

GCCATCCCAA GCCGTGAAGC AACTGCACTT TTTCGTCGAG CGTCATCTGC TGGATGACCA      300

GATCAGCCCG CTCATCCGGA GAGAGATATT TGTTTCCCA  TGGGCGTATG GGCCCGGTAT     360

TTATGGGCTG TCCGAATTGC GTGTAGATTG GAGCCGAGGC GGCAAGAAAG AGGAACGCCA      420

GTAGGAGATT CGCTGCTTTC AGCAAAGACC TGCGCATAAT CATCTATCGT GCTCCATAAA      480

CCTCGTCAGA CCGATCAGCT CCTATCGTTT CGGTTTTGGT TCCTTGTGCA CCATCGCAAC      540

CATCGCAACA GGCCACCAGA TCACCCGCTG CGCGCCTGCG CTTGTAGGCA ATGAGGTTCG      600

GCTTCG                                                                 606
```

( 2 ) INFORMATION FOR SEQ ID NO:14:

( i ) SEQUENCE CHARACTERISTICS:
        ( A ) LENGTH: 605 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: T1689

( x i ) SEQUENCE DESCRIPTION: SEQ ID NO:14:

```
CTCGGTGCCG ATGAGGTCGC CGTATTCGTA GGCGATTTCG GGATCCCAGC TCGAGGCCTC      60
GGCCACACCG GAAGGCAGCG CCGTGGAATA GCGGCTACGC GGTGCTCCAC GGGCAACACC     120
AACGGCGGCA TCGGACATCT GCAGGTCAGG AATCCCCAAG CGTTCAATAC CGGGAATAAA     180
ACCCGCGCCC CCAAGAGAAC GCACGCCAGG CACTGACGTG GTTCCCTCAA GGAGAGTCCG     240
CCATCCCAAG CCGTGAAGCA ATTGCACTTT TCGTCGAGC GTCATCTGCT GGATGACCAG      300
ATCGGCCCGC TCATCAGGAG AGAGGTATTT GTTTTCCCAT GGGCGTTCGG GTGCGGCATT     360
TACTGGTTGT CTGAATTGCG TGTACATTGG GGCCGAGGCG ACAAGAAAGA AGAATGCCAG     420
TATTAAATTA GCTGCTTTCA GCAGGGACCT GCGCAGAATC ATCGATTGCG CTCCAGAAAT     480
CTCGTCAGAT CGATCAGCTC CTCCGTTTCG GTTTGGCTT CCTGGGAAAT CATCGACCAT      540
CGCGGCCGGC CGAACCAGAT CACGTGCTCC GAGCTTGCGC TCGTAGGCAA TGAGGTTCGG     600
CTTCG                                                                 605
```

( 2 ) INFORMATION FOR SEQ ID NO:15:

( i ) SEQUENCE CHARACTERISTICS:
        ( A ) LENGTH: 604 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: T10892

( x i ) SEQUENCE DESCRIPTION: SEQ ID NO:15:

```
CTCGGTGCCG ATGTGGTCGC CGTATTCGTA GGCGATTTCG GGATCCCAGC TCGAGGCCTC      60
GGCCACACCG GAAGGCAGCG CCGTGGAATA GCGGCTACGC GGTGCTCCAC GGGCAACACC     120
AACGGCGGCA TCGGACATCT GCAGGTCAGG AATCCCCAAG CGTTCAATAC CGGGAATAAA     180
ACCCGCGCCC CCAAGAGAAC GCACGCCAGG CACTGACGTG GTTCCCTCAA GGAGAGTCCG     240
CCATCCCAAG CCGTGAAGCA ATTGCACTTT TCGTCGAGC GTCATCTGCT GGATGACCAG      300
ATCGGCCCGC TCATCAGGAG AGAGGTATTT GTTTTCCCAT GGGCGTTCGG GTGCGGCATT     360
TACTGGTTGT CTGAATTGCG TGTACATTGG GGCCGAGGCG ACAAGAAAGA AGAATGCCAG     420
TATTAAATTA GCTGCTTTCA GCAGGGACCT GCGCAGAATC ATCGATTGCG CTCCAGAAAT     480
CTCGTCAGAT CGATCAGCTC CTCCGTTTCG GTTTGACTT CCTGGGAAAT CATCGACCAT      540
CGCGGCCGGC CGAACCAGAT CACGTGCTCC GAGCTTGCGC TCGTGGCAAT GAGGTTCGGC     600
TTCG                                                                  604
```

( 2 ) INFORMATION FOR SEQ ID NO:16:

23

( i ) SEQUENCE CHARACTERISTICS:
  ( A ) LENGTH: 602 base pairs
  ( B ) TYPE: nucleic acid
  ( C ) STRANDEDNESS: double
  ( D ) TOPOLOGY: linear ( i i ) MOLECULE TYPE: DNA (genomic)

( v i ) ORIGINAL SOURCE:
  ( B ) STRAIN: T18492

( x i ) SEQUENCE DESCRIPTION: SEQ ID NO:16:

| | | | | | |
|---|---|---|---|---|---|
| CTCGGTGCCG | ATGTGGTTGC | CGTATTCGTA | TGCGATTTCC | TGGATCCCAG | CTCGAGGCTT  60 |
| CAGCCACGCC | GGAAGGCAGC | GCCGTGGAAT | AGCGGCTACG | CGGGCTCCA  | CGCGCAACAC  120 |
| CAACGGCGGC | ATCGGACATC | TGCAGGTCTG | GAATCCCCAA | GCGCTCGATA | CCGGGGATGA  180 |
| AACCCGCGCC | CCAAGAGAG  | CGCACACCAG | GCACTGACGT | GGTTCCCTCA | AGAAGGATCC  240 |
| GCCATCCCAA | GCCGTGAAGC | AACTGCACTT | TTTCGTCGAG | CGTCATCTGC | TGGATGACCA  300 |
| GATCAGCCCG | CTCATCCGGA | GAGAGATATT | TGTTTTCCCA | TGGGCGTATG | GGCCCGGTAT  360 |
| TTATGGGCTG | TCCGAATTGC | GTGTAGATTG | GAGCCGAGGC | GGCAAGAAAG | AGGAACGCCA  420 |
| GTAGGAGATT | CGCTGCTTTC | AGCAAAGACC | TGCGCATAAT | CATCTATCGG | TGCTCCATAA  480 |
| ACCTCGTCAG | ACCGATCAGC | TCCTATCGTT | TCGGTTTTGN | TTCCTTGTGC | ACCATCGACC  540 |
| ATCGCAACCA | GCCACCAGAT | CACCCGCTGC | GCGCCTGCGC | TTGGCAATGA | GGTTCGGCTT  600 |
| CG | | | | |  602 |

( 2 ) INFORMATION FOR SEQ ID NO:17:

( i ) SEQUENCE CHARACTERISTICS:
  ( A ) LENGTH: 605 base pairs
  ( B ) TYPE: nucleic acid
  ( C ) STRANDEDNESS: double
  ( D ) TOPOLOGY: linear ( i i ) MOLECULE TYPE: DNA (genomic)

( v i ) ORIGINAL SOURCE:
  ( B ) STRAIN: T11792

( x i ) SEQUENCE DESCRIPTION: SEQ ID NO:17:

| | | | | | |
|---|---|---|---|---|---|
| CTCGGTGCCG | ATGAGGTCCC | CGTATTCGTA | GGCGATTTCG | GGATCCCAGC | TCGAGGCCTC  60 |
| GGCCACACCG | GAAGGCAGCG | CCGTGGAATA | GCGGCTACGC | GGTGCTCCAC | GGGCAACACC  120 |
| AACGGCGGCA | TCGGACATCT | GCAGGTCAGG | AATCCCCAAG | CGTTCAATAC | CGGGAATAAA  180 |
| ACCCGCGCCC | CAAGAGAAC  | GCACGCCAGG | CACTGACGTG | GTTCCCTCAA | GGAGAGTCCG  240 |
| CCATCCCAAG | CCGTGAAGCA | ATTGCACTTT | TCGTCGAGC  | GTCATCTGCT | GGATGACCAG  300 |
| ATCGGCCCGC | TCATCAGGAG | AGAGGTATTT | GTTTTCCCAT | GGGCGTTCGG | GTGCGGCATT  360 |
| TACTGGTTGT | CTGAATTGCG | TGTACATTGG | GGCCGAGGCG | ACAAGAAAGA | AGAATGCCAG  420 |
| TATTAAATTA | GCTGCTTTCA | GCAGGGACCT | GCGCAGAATC | ATCGATTGCG | CTCCAGAAAT  480 |
| CTCGTCAGAT | CGATCAGCTC | CTCCGTTTCG | GTTTGACTT  | CCTGGGAAAT | CATCGACCAT  540 |
| CGCGGCCGGC | CGAACCAGAT | CACGTGCTCC | GAGCTTGCGC | TCGTGGGCAA | TGAGGTTCGG  600 |
| CTTCG | | | | |  605 |

( 2 ) INFORMATION FOR SEQ ID NO:18:

( i ) SEQUENCE CHARACTERISTICS:
  ( A ) LENGTH: 605 base pairs
  ( B ) TYPE: nucleic acid
  ( C ) STRANDEDNESS: double (D) TOPOLOGY: linear (ii) MOLECULE TYPE: DNA (genomic)

(vi) ORIGINAL SOURCE:
  (B) STRAIN: 5C8246

(xi) SEQUENCE DESCRIPTION: SEQ ID NO:18:

| | | | | | | |
|---|---|---|---|---|---|---|
| CTCGGTGCCG | ATGAGGTCAC | CGTATTCGTA | GGCGATTTCG | GGATCCCAGC | TCGAGGCCTC | 60 |
| GGCCACACCG | GAAGGCAGCG | CCGTGGAATA | GCGGCTACGC | GGTGCTCCAC | GGGCAACACC | 120 |
| AACGGCGGCA | TCGGACATCT | GCAGGTCAGG | AATCCCCAAG | CGTTCAATAC | CGGGAATAAA | 180 |
| ACCCGCGCCC | CCAAGAGAAC | GCACGCCAGG | CACTGACGTG | GTTCCCTCAA | GGAGAGTCCG | 240 |
| CCATCCCAAG | CCGTGAAGCA | ATTGCACTTT | TTCGTCGAGC | GTCATCTGCT | GGATGACCAG | 300 |
| ATCGGCCCGC | TCATCAGGAG | AGAGGTATTT | GTTTTCCCAT | GGGCGTTCGG | GTGCGGCATT | 360 |
| TACTGGTTGT | CTGAATTGCG | TGTACATTGG | GGCCGAGGCG | ACAAGAAAGA | AGAATGCCAG | 420 |
| TATTAAATTA | GCTGCTTTCA | GCAGGGACCT | GCGCAGAATC | ATCGATTGCG | CTCCAGAAAT | 480 |
| CTCGTCAGAT | CGATCAGCTC | CTCCGTTTCG | GTTTGACTT | CCTGGGAAAT | CATCGACCAT | 540 |
| CGCGGCCGGC | CGAACCAGAT | CACGTGCTCC | GAGCTTGCGC | TCGTAGGCAA | TGAGGTTCGG | 600 |
| CTTCG | | | | | | 605 |

(2) INFORMATION FOR SEQ ID NO:19:

(i) SEQUENCE CHARACTERISTICS:
    (A) LENGTH: 540 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (B) STRAIN: T8594

(xi) SEQUENCE DESCRIPTION: SEQ ID NO:19:

| | | | | | | |
|---|---|---|---|---|---|---|
| GTATGCGATT | TCTGGATCCC | AGCTCGAGGC | TTCAGCCACA | CCGGACGGCA | GCGCCGTAGA | 60 |
| ATAGCGGCTC | CGTGGGGCTC | CGCGCGCGAC | GCCAAGGGCG | GCATCCGACA | TCTGCAGGTC | 120 |
| GGGAATCCCC | AAACGCTCAA | TACCCGGGNT | GAAACCCGCG | CCTCCAAGAG | AACGCACGCC | 180 |
| CGGCCCGGAC | GTGGTTCCGT | CAAGGTAAAC | TCGCCATCCC | AGGCCATGAA | GCAACTGCAC | 240 |
| TTTTCGTCG | AGCGTCATCT | GCTGGATGAC | CAGATCGGCC | CGCTCATCCG | GGGAAAGTAA | 300 |
| TTTGTTTGTC | CATGGCCGTT | TGGGTTGCGG | TATTTACTGG | CTGTCCGAAT | TGCNTTTTAC | 360 |
| ATTGGANCCG | AAGCGAACAA | AAAAAGAAAA | AATGCCCATT | AGGAAATTAA | CTGCTGTTCA | 420 |
| NCNAAAGGCC | TGCNCAAATC | ATCTATCCNT | GCNCCCANAA | TCCCTTCAGG | TTCAAAAAAT | 480 |
| AACCCTTTCC | GGTTTTAAC | TNCCCTTGAA | AACCATCAAC | ACGGANCCCC | AATTNNGNGT | 540 |

(2) INFORMATION FOR SEQ ID NO:20:

(i) SEQUENCE CHARACTERISTICS:
    (A) LENGTH: 558 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (B) STRAIN: T9294

(xi) SEQUENCE DESCRIPTION: SEQ ID NO:20:

```
GTATGCGATT TCTGGATCCC AGCTCGAGGC TTCAGCCACA CCGGACGGCA GCGCCGTAGA      60
ATAGCGGCTC CGTGGGGCTC CGCGCGCGNC GCCAAGGGCG GCATCCGACA TCTGCAGGTC     120
GGGNATCCCC AAACGCTCAA TACCCGGGNT GAAACCCGCG CCTCCAAGNG NACGCACGCC     180
CGGCCCGGAC GTGGTTCCGT CAAGGTAAAC TCGCCATCCC AGGCCATGAA GCAACTGCAC     240
TTTTTCGTCG AGCGTCATCT GCTGGATGAC CAGATCGGCC CGCTCATCCG GGGAAAGTAA    300
TTTGTTTGTC CATGGCCGTT TGGGTGCGGT ATTTACTGGC TGTCCGAATT GCGTGTACAT     360
TGGAGCCGAG GCGACAAGAA AGAAGAATGC CAGTAGGAAA TTAGCTGCTG TCAGCAAAGG    420
CCTGCGCAGA ATCATCTANC GTGCTCCATA AANCNCGTCA GGTCGATCAG CTACTCGTTT    480
CGGTTTTTAC TTNCCTTGAA AACCATCGAC CACGGCAGCC AGCCGCCAGA CCACGTGCTC    540
CGAGCTTGCG CTTGTAGG                                                   558
```

( 2 ) INFORMATION FOR SEQ ID NO:21:

( i ) SEQUENCE CHARACTERISTICS:
        ( A ) LENGTH: 705 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:21:

```
CGTCATGCTG AAGTCCCTGG TCGCGWARCT CGGTGCCGAT GWGGTYVCCG TATTCGTAKG     60
CGATTTCCKG GATCCCAGCT CGAGGCYTCA GSCCACRCCG GAAGGCAGCC SCCGTGGAAT    120
AGCGGCTACG CGGKGCTCCA CGSGCAACAC CAACGGCGG ATCGGACATC TGCAGGTCDG     180
GAATCCCCAA GCGYTCRATA CCGGGRATRA AACCCGCGCC CCAAGAGRR CGCACRCCAG     240
GCACTGACGT GGYTCCCTCA AGRAGRRTCC GCCATCCAA GCCGTGAAGC AAYTGCACTT     300
TTTCGTCGAG CGTCATCTGC TGGATGACCA GATCRGCCCG CTCATCMGGA GAGAGRTATT   360
TGTTTTCCCA TGGGCGTWYG GGYSCGGYAT TTAYBGGYTG TCYGAATTGC GTGTASATTG    420
GRGCCGAGGC GRCAAGAAAG ARGAAYGCCA GTAKKARATT MGCTGCTTTC AGCARRGACC    480
TGCGCAKAAT CATCKATYGG YGCTCCAKAA AYCTCGTCAG AYCGATCAGC TCCTAYCGTT    540
TCGGTTTTGR NTTCCTKGGA AATCATSSAC CATCGCRRCC ATSGCAACSA GGCCACCAGA    600
TCACSYGCTS CGMGCYTGCG CTYGTRGGCA ATGAGGTTCG GCTTCGCCCG KTCTCCAGTA   660
AAGRGCCTTT GRCCCTGATG CGTTTCCAGA GTGCCAGGAG ACAGA                    705
```

( 2 ) INFORMATION FOR SEQ ID NO:22:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
GGATCCCAGC TCGAGGC                                                    17
```

( 2 ) INFORMATION FOR SEQ ID NO:23:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
CGATTCCGCT CCAGACTTCT CGGGTGCACT TTTTCGTCGA                    40
```

( 2 ) INFORMATION FOR SEQ ID NO:24:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
CGATTGGGCT CCAGACTTCT CGGGTGCACT TTTCGTCG                      39
```

( 2 ) INFORMATION FOR SEQ ID NO:25:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
CGATTGGGCT CCAGACTTCT CGGGGCACTT TTTCGTCG                      38
```

( 2 ) INFORMATION FOR SEQ ID NO:26:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
ACCGCATCGA ATGCATGTCT CGGGTCTCCG GATGAGCG                      38
```

( 2 ) INFORMATION FOR SEQ ID NO:27:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
ACGGCATCGA ATGCATGTCT CGGGCCGGAT GAGCGGG                       37
```

( 2 ) INFORMATION FOR SEQ ID NO:28:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

```
ACGGCATCGA ATGCATGTCT CGGGCGGATG AGCGGG                        36
```

( 2 ) INFORMATION FOR SEQ ID NO:29:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

```
ATCCCAAGCC GTGA                                                14
```

( 2 ) INFORMATION FOR SEQ ID NO:30:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CCCAAACGCC CATG 14

( 2 ) INFORMATION FOR SEQ ID NO:31:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

CCCAAGCCGT GAAG 14

( 2 ) INFORMATION FOR SEQ ID NO:32:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

CCAAGCCGTG AAG 13

( 2 ) INFORMATION FOR SEQ ID NO:33:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

CCAGGCCATG AAG 13

( 2 ) INFORMATION FOR SEQ ID NO:34:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

CAAACGCCCA TGG 13

( 2 ) INFORMATION FOR SEQ ID NO:35:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

TCATCTGCTG GATG 14

( 2 ) INFORMATION FOR SEQ ID NO:36:

```
    ( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:36:

GATCTGGTCA TCCAG                                                                        15

( 2 ) INFORMATION FOR SEQ ID NO:37:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:37:

TCATCTGCTG GATGAC                                                                       16

( 2 ) INFORMATION FOR SEQ ID NO:38:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:38:

GATCTGGTCA TCCAGC                                                                       16

( 2 ) INFORMATION FOR SEQ ID NO:39:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:39:

GTCATCCAGC AGATGA                                                                       16

( 2 ) INFORMATION FOR SEQ ID NO:40:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:40:

GCTGGATGAC CAGATC                                                                       16
```

MATERIALS AND METHODS FOR SPECIES-SPECIFIC DETECTION OF MYCOBACTERIUM KANSASII NUCLEIC ACIDS

FIELD OF THE INVENTION

The present invention relates to oligonucleotide sequences and methods for detection and/or identification of microorganisms using nucleic acid amplification and nucleic acid hybridization.

BACKGROUND OF THE INVENTION

The mycobacteria are a genus of bacteria which are acid-fast, non-motile, gram-positive rods. The genus comprises several species which include, but are not limited to, *Mycobacterium africanum, M. avium, M bovis, M bovis-BCG, M. chelonae, M. fortuitum, M. gordonae, M. intracellulare, M. kansasii, M. microti, M. scrofulaceum, M. paratuberculosis* and *M. tuberculosis*. Certain of these organisms are the causative agents of disease. For the first time since 1953, cases of mycobacterial infections are increasing in the United States. Of particular concern is tuberculosis, the etiological agent of which is *M. tuberculosis*. Many of these new cases are related to the AIDS epidemic, which provides an immune compromised population which is particularly susceptible to infection by mycobacteria. However, other mycobacterial infections are also increasing as a result of the increase in numbers of immune compromised patients. *Mycobacterium avium, Mycobacterium kansasii* and other non-tuberculosis mycobacteria are found as opportunistic pathogens in HIV infected and other immune compromised patients.

Conventional diagnosis of mycobacterial infections relies on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one to two weeks. However, there is still a need to reduce the time required for diagnosing mycobacterial infections to less than a week, preferably to about one day. Oligonucleotide probe based assays such as Southern hybridizations or dot blots are capable of returning a rapid result (i.e., in one day or less). Assays based on amplification of nucleic acids are usually more sensitive and may provide even more rapid results, often within hours. For diagnosis of mycobacterial infections such methods require development of oligonucleotide probes or primers which are specific for the genus *Mycobacterium* or specific for a particular species of mycobacteria if species identification of the organism is desired.

Conventional laboratory identification of *Mycobacterium kansasii* is based upon biochemical testing and determination of growth characteristics. These include catalase production, urease activity, TWEEN hydrolysis, nitrate reduction and the ability of the bacterium to produce pigment when exposed to light (photochromogenicity). Because several other mycobacterial species exhibit a similar biochemical profile, photochromogenicity is generally relied upon for conclusive identification of *Mycobacterium kansasii*. However, determination of photochromogenicity requires a pure culture of the organism and this phenotype can be variable, subjective and difficult to determine reliably. For these reasons, there have been attempts to identify *Mycobacterium kansasii* by species-specific hybridization or nucleic acid amplification using oligonucleotide probes. Z. H. Huang, et al. (1991. J Clin. Microbiol 29, 2125–2129) have reported a DNA probe obtained from a genomic library with a degree of species-specificity for *Mycobacterium kansasii*. This clone (pMK1–9) showed some cross-hybridization with other species, including *M. gastri*, and did not detect a genetically distinct subgroup of *M. kansasii*. The nucleotide sequence of pMK1–9 was not reported, nor was the gene from which it may have been derived identified. B. C. Ross, et al. (1992. J. Clin. Microbiol 30, 2930–2933) also reported identification of genetically distinct subspecies of *M. kansasii* using the pMK1–9 probe, a 65 kDa antigen gene probe and a commercial DNA probe test employing probes which specifically hybridize to rRNA (ACCU-PROBE, Gen-Probe, San Diego, Calif.). The ACCU-PROBE was also evaluated by E. Tortoli, et al. (1994. Eur. J. Clin. Microbiol Infect Dis. 13, 264–267) and found to have 100% specificity but only 72.8% sensitivity, apparently as a result of the genetic heterogeneity of *M. kansasii*. T. Rogall, et al. (1990. J. Gen. Microbiol 136, 1915–1920) used the 16S rRNA sequence in a polymerase chain reaction (PCR) based sequencing strategy for identification of mycobacterial species. However, these primers could not be used to differentiate *M. gastri* from *M. kansasii* because the 16S rRNA sequence from these two species is identical in spite of their differing phenotypic characteristics. Similar studies have been published by B. B öddinghaus, et al. (1990. J. Clin. Microbiol 28, 1751–1759), who reported oligonucleotides derived from 16S rRNA sequences which are specific for the *M. tuberculosis* group, i.e., *M. avium-M. paratuberculosis*, and *M. intracellulare*. M. Yang, et al. (1993. J Clin. Microbiol 31, 2769–2772) have reported isolation of a sequence from a clinical isolate which, when used as a hybridization probe, exhibits *M. kansasii* species-specificity. This probe (p6123) hybridized to all *M. kansasii* strains tested, including the subgroup which is pMK1–9 negative. U.S. Pat. No. 5,500,341 describes *M. kansasii*-specific amplification primers which are derived from p6123.

The following terms are defined herein as follows:

An amplification primer is an oligonucleotide for amplification of a target sequence by extension of the oligonucleotide after hybridization to the target sequence or by ligation of multiple oligonucleotides which are adjacent when hybridized to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 3' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. PNAS 89:392–396 and 1992 Nucl Acids Res. 20:1691–1696). The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. Its length and sequence are generally not critical and may be routinely selected and modified to obtain the desired $T_m$ for hybridization. As the target binding sequence is the portion of a primer which determines its target-specificity, for amplification methods which do not require specialized sequences at the ends of the target the amplification primer generally consists essentially of only the target binding sequence, e.g., as in PCR or the Ligase Chain Reaction (LCR). For amplification methods other than SDA which require specialized sequences appended to the target (e.g., an RNA polymerase promoter for 3SR, NASBA or transcription based amplification), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The term probe refers to an oligonucleotide which hybridizes to a target sequence, typically to facilitate its detection. The probe is not extended by polymerase. Probes are typically at least about 10 nucleotides in length to ensure the desired hybridization specificity, but may be of any length which retains the desired specificity. For convenience, however, probes are usually from about 10 to about 75 nucleotides in length, preferably about 15 to about 50 nucleotides long. The probe is often linked to a detectable label to facilitate its detection or capture when hybridized to the target sequence, thus facilitating detection of the target sequence. It should be understood, however, that primers and probes in many cases may be structurally similar or even identical. The terms primer and probe refer to the function of the oligonucleotide. That is, a hybridized oligonucleotide may function as a probe if it is used to capture or detect a target sequence, and the same oligonucleotide may function as a primer if it is used to amplify the target (e.g., by extension of the hybridized oligonucleotide on the target or by ligation of multiple adjacent oligonucleotides hybridized to the target). A primer may also be used to detect a target sequence if the detection method employs extension of the oligonucleotide after it is hybridized to the target.

The terms target or target sequence refer to nucleic acid sequences to be amplified. These include the original nucleic acid sequence to be amplified and its complementary second strand as well as either strand of a copy of the original target sequence generated during the amplification reaction.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization in a species of organism or a group of related species without substantial detection, amplification or oligonucleotide hybridization in other species of the same genus or species of a different genus.

Identical sequences will hybridize to the same complementary nucleotide sequence. Substantially identical sequences are sufficiently similar in their nucleotide sequence that they also hybridize to the same nucleotide sequence.

The term assay probe refers to any oligonucleotide used to facilitate detection or identification of a nucleic acid. For example, in the present invention, assay probes are used for detection or identification of *Mycobacterium kansasii* nucleic acids. Detector probes, detector primers, capture probes and signal primers as described below are examples of assay probes.

The abbreviation "LCDC" in the *M. kansasii* strain designations indicates the Laboratory of Canadian Disease Control, and the abbreviation "TMC" indicates the Trudeau Mycobacteria Collection. Many of the strains obtained from the TMC are now also available from the American Type Culture Collection.

SUMMARY OF THE INVENTION

The present invention provides a newly-identified fragment of the *M. kansasii* genome which is *M. kansasii*-specific (i.e., species-specific) in nucleic acid hybridization assays. Sequencing of the fragment and searches for homology to known sequences revealed that neither the full-length fragment (designated herein as "KATS1") or any subsequences of KATS1 consisting of 10 consecutive nucleotides have been previously identified. Primers and probes derived from the KATS1 nucleotide sequence are therefore highly species-specific for *M. kansasii* and those derived from the most highly conserved regions detect both typical and atypical strains. Oligonucleotides derived from KATS1 are sensitive and specific for detection of both typical and atypical *M. kansasii* with potentially fewer false negatives than probes and primers of the prior art.

DETAILED DESCRIPTION OF THE INVENTION

The KATS1 DNA fragment was identified using Arbitrarily Primed PCR (AP-PCR, J. Welsh, et al. 1990. Nucl. Acids Res. 18, 7213–7218) to create a differential display of amplification products from *M. kansasii* strains TMC1201 and LCDC724 (typical and atypical, respectively), *M. tuberculosis* (H37Rv), *M. avium* (CDC33) and *M. intracellulare* (ATCC 13950). The AP-PCR primers were: CGTCATGCT-GAAGTCCCT (SEQ ID NO:1) and TCTGTCTCCTG-GCACTCT (SEQ ID NO:2). Fifty µl reactions containing 10 mM TRIS-HCL pH 8.3, 50 mM KCl, 1.5 mM $MgCl_2$, 0.001% (w/v) gelatin, 0.2 mM dNTPs, 3.5 µM $^{32}$P-labeled SEQ ID NO:1, 3.5 µM $^{32}$P-labeled SEQ ID NO:2, 1 ng genomic DNA template and 2.5 U Taq DNA polymerase were prepared and the targets were amplified in a Perkin Elmer Cetus thermocycler (Model 480). After denaturing at 95° C. for 3 min. the amplification reaction was cycled 40 times through the following profile: 94° C., 1 min.; 37° C., 2 min.; 72° C., 2 min. Following thermocycling, the samples were heated at 72° C. for 7 min. and stored at 4° C. overnight. Amplification products for each species or strain were visualized by autoradiography after electrophoresis on 8% denaturing acrylamide gels (100 W).

A unique band which was present in both *M. kansasii* strains but absent in non-*M. kansasii* species was identified and designated KATS1. The KATS1 band was excised from the gel and the DNA was extracted by boiling in 100 µl, distilled sterile water for 15 min. and ethanol precipitation. Five µl of the extracted DNA was re-amplified by PCR as before, using the following thermocycling profile: 94° C., 1 min.; 60° C., 2 min.; 72° C., 2 min. for 35 cycles.

The species-specificity of the KATS1 fragment was tested by hybridization to the genomic DNA of various strains of *M. kansasii* and various non-*M. kansasii* mycobacteria. One μg of the genomic DNA of each organism (*M. kansasii* TMC1201, *M kansasii* LCDC711, *M. kansasii* LCDC715, *M. kansasii* LCDC724, *M. avium* ATCC25291, *M. intracellulare* TMC1406, *M. tuberculosis* H37Rv, *M. fortuitum* ATCC6841, *M. scrofulaceum* ATCC19981 and *M. haemophilum* ATCC27548) was denatured and blotted on a ZETA-PROBE GT membrane (Bio-Rad). The KATS1 fragment was labeled by random primed labeling (commercially available in kit form from Boehringer Mannheim) and used as a hybridization probe. Hybridization conditions were as recommended by the manufacturer of the membrane. All of the *M. kansasii* strains tested were clearly positive for hybridization to the KATS1 probe, whereas all of the non-*M. kansasii* species were clearly negative.

The KATS1 fragment was then cloned into the PCR TA II vector (Invitrogen) according to the manufacturer's instructions. The presence of the KATS1 insert was confirmed by restriction digestion with EcoRI, which released a DNA fragment approximately 650 base pairs in length. The species-specificity of the cloned KATS1 fragment was then retested by dot blot hybridization as described above. The six *M. kansasii* strains tested (including LCDC714 and LCDC725 in addition to those previously tested) were all clearly positive, confirming the utility of KATS1 as a probe to detect both typical and atypical strains. The fifteen non-*M. kansasii* species tested were all clearly negative (including all species previously tested except *M. haemophilum* and the following additional species: *M. avium* CDC33, *M. avium* CDC16, *M. chelonae* TMC1543, *M. gastri* LCDC1301, *M. intracellulare* ATCC13950, *M. intracellulare* LCDC1705, *M. marinum* LCDC801, *M. simiae* CDC2, *M. smegmatis* TMC1533 and *M. tuberculosis* VA44). All of the non-mycobacterial species tested were also clearly negative for hybridization to KATS1 (*A. israelii* ATCC10049, *C. diphtheriae* ATCC11931, *N. asteroides* ATCC3308, *P. acnes* ATCC6919, *R. rhodochrous* ATCC13808 and *S. somaliensis* ATCC13201).

*E. coli* transformed with the plasmids containing the KATS1 DNA fragments from both the typical strain of *M. kansasii* (TMC1201) and the atypical strain (LCDC724) were deposited with the American Type Culture Collection (Rockville, Md.) on Jun. 27, 1996, as Accession No. 98092 (containing plasmid KATS1-1201) and Accession No. 98091 (containing plasmid KATS1-724). After cloning, these KATS1 DNA fragments were sequenced using primers designed for the T7 and SP6 promoters located in the PCR TA II vector. Sequencing was performed using a ABI PRISM Terminator cycle sequencing kit (Perkin Elmer), a Perkin-Elmer Cetus thermocycler Model 480 and a Model 373 DNA sequencer (Applied Biosystems) according to the protocols recommended by the manufacturers. The KATS1 sequences obtained for the two strains are shown in SEQ ID NO:3 (LCDC724) and SEQ ID NO:4 (TMC1201). They were aligned to identify regions of homology and to determine a consensus sequence for KATS1 in these two species (SEQ ID NO:5). KATS1 has a base composition which is approximately 58% GC. Typical and atypical strains share approximately 90% homology, with the 5' portion of the fragment being more homologous than the 3' portion. Among the 555 sequence entries for mycobacteria in GENBANK, no sequence homologous to KATS1 was found. Similarly, a search in GENBANK, GENESEQ and EMBL databases for homology to non-mycobacterial sequences revealed no matches. A GENBANK search using TMC 1201 KATS1 subsequences of 10 consecutive nucleotides (shifting the 10 nucleotide "window" one nucleotide for each subsequent sequence search) also revealed no matches. It is therefore expected that any oligonucleotide consisting of about 10 or more consecutive nucleotides in the KATS1 sequence or its complement would be *M. kansasii*-specific when used as an assay probe or as the target binding sequence of an amplification primer. A search for reading frames in KATS1 suggested that this DNA fragment does not encode a protein.

KATS1-specific PCR primers were designed based on the sequence analysis of TMC1201 and LCDC724. The 3' primer was CGAAGCCGAACCTCATTG (SEQ ID NO:6) and the two alternative 5' primers were CTCGGTGCCGATGAGGT (SEQ ID NO:7) and CCGATGAGGTTGCCGTATTCG (SEQ ID NO:8). SEQ ID NO:6 and SEQ ID NO:7 were used to amplify all strains except T9294 and T8594, which are environmental isolates. These two strains were amplified using SEQ ID NO:6 and SEQ ID NO:8, as the binding site of SEQ ID NO:7 is in a region which is less highly conserved in atypical strains. PCR was performed essentially as described for the reamplification of KATS1 above, using the following strains of *M. kansasii* as sources of genomic DNA: TMC1201, LCDC711, LCDC714, LCDC715, LCDC724, LCDC725, T1492, T1689, T10892, T18492, T11792, 5C8246, T8594 and T9294. KATS1 was successfully amplified in all fourteen strains of *M. kansasii*, including both typical and atypical strains.

The KATS1 amplification products (except those of LCDC715 and LCDC 725) were then sequenced as described above. The sequences were determined by multiple sequencing reactions employing internal and external sequencing primers:

Internal primers

CAAGAAGGATCCGCCATCCC, SEQ ID NO:9

ACGCCCATGGGAAAACAAA, SEQ ID NO:10

External primers

SEQ ID NO:6, SEQ ID NO:7 and SEQ ID NO:8

Ten additional KATS1 sequences were thus obtained (SEQ ID NOs:11–20). Seven (LCDC711, LCDC714, T1689, T10892, T18492, T11792 and 5C8246) were aligned with TMC 1201 and LCDC 724, and showed about 80% homology. A consensus sequence sequence for these nine strains was determined (SEQ ID NO:21).

The species-specificity of KATS1 and its subsequences of at least about 10 consecutive nucleotides was confirmed by PCR in a broader range of typical and atypical strains of *M. kansasii*. The 50 μl reaction mixtures and the PCR profile were the same as used for reamplification of KATS1, except that 2.0 μM of each primer and 10 ng of template DNA were present. Forty-seven strains of *M. kansasii* were each amplified in two PCRs. Each PCR reaction used one of two different primer pairs selected from SEQ ID NO:6/SEQ ID NO:8, SEQ ID NO:9/SEQ ID NO:10 and SEQ ID NO:6/ SEQ ID NO:22 (GGATCCCAGCTCGAGGC) as shown below:

| SEQ ID NO:6/SEQ ID NO:7 and SEQ ID NO:9/SEQ ID NO: 10 | | |
|---|---|---|
| TMC1201 | LCDC711 | LCDC714 |
| LCDC715 | LCDC724 | LCDC725 |
| T1492 | T1689 | T10892 |
| T18492 | T11792 | 5C8246 |
| T8594 | T9294 | |
| SEQ ID NO:22/SEQ ID NO:6 and SEQ ID NO:9/SEQ ID NO: 10 | | |
| TMC1201 | 12478 | 2256 |
| 2237 | 2205 | T10592 |
| T1085 | T10992 | T11292 |

| | | |
|---|---|---|
| T1185 | T190 | T2692 |
| T285 | T4392 | T4492 |
| T4693 | T4791 | T485 |
| T5 | T5295 | T5993 |
| T6093 | T686 | T7193 |
| T785 | T8394 | T8794 |
| T8894 | T9094 | T9194 |
| T9494 | T994 | T186 |

Amplification was clearly positive with both primer pairs in all typical and atypical strains except T9094 and T994, confirming the high degree of species-specificity of KATS1 and primers/probes derived from KATS1. T9094 and T994 were negative with one primer pair (SEQ ID NO:9/SEQ ID NO:10) but positive with the other (SEQ ID NO:6/SEQ ID NO:22). Although the KATS1 fragment of these two strains was not sequenced, SEQ ID NO:9 is in a slightly variable region in other atypical strains. Substitution of another primer in a more conserved region should resolve such occasional amplification failures.

Similar amplification reactions were used to evaluate cross-reactivity in twenty-two non-*M. kansasii* species of mycobacteria and six closely related non-mycobacteria: *M. avium* ATCC25291, *M. avium* CDC33, *M. chelonae* TMC1543, *M. fortuitum* ATCC6841, *M. gastri* LCDC1301, *M. gordonae* TMC1318, *M. gordonae* ATCC14470, *M. intracellulare* ATCC13950, *M. intracellulare* LCDC1705, *M. marinum* LCDC801, *M. microti* LCDC203, *M. scrofulaceum* BDDIS2404, *M. simiae* CDC2, *M. smegmatis* TMC1533, *M. tuberculosis* H37Rv, *M. tuberculosis* VA44, *A. israelii* ATCC10049, *C. diphtheriae* ATCC11931, *N. asteroides* ATCC3308, *P. acnes* ATCC6919, *R. rhodochrous* ATCC13808 and *S. somaliensis* ATCC13201. Genome targets were amplified in PCR reactions as before, using both the SEQ ID NO:6/SEQ ID NO:8 and SEQ ID NO:9/SEQ ID NO:10 primer pairs. No amplification products were detected in any of the samples, confirming the species-specificity of KATS1 and primer/probes derived from KATS1.

Primers and probes for use in SDA were also designed based on the KATS1 sequence and tested in amplification reactions for species-specificity, cross-reactivity and sensitivity. The primers and probes are shown in the following table. The restriction endonuclease recognition site (in this example BsoBI) is bolded and the target binding sequences of the amplification primers are italicized.

Upstream amplification primers
SEQ ID NO:23
  CGATTCCGCTCCAGACTTCTCGGGTG-CACTTTTTCGTCGA
SEQ ID NO:24
  CGATTGGGCTCCAGACTTCTCGGGTG-CACTTTTTCGTCG
SEQ ID NO:25
  CGATTGGGCTCCAGACT-TCTCGGGGCACTTTTTCGTCG Downstream amplification primers
SEQ ID NO:26
  ACCGCATCGAATGCATGTCTCGGGTCTC-CGGATGAGCG
SEQ ID NO:27
  ACGGCATCGAATGCATGTCTCGGGCCG-GATGAGCGGG
SEQ ID NO:28
  ACGGCATCGAATGCATGTCTCGGGCG-GATGAGCGGG Bumper primers (left and right)
SEQ ID NO:29
  ATCCCAAGCCGTGA
SEQ ID NO:30
  CCCAAACGCCCATG
SEQ ID NO:31
  CCCAAGCCGTGAAG
SEQ ID NO:32
  CCAAGCCGTGAAG
SEQ ID NO:33
  CCAGGCCATGAAG
SEQ ID NO:34
  CAAACGCCCATGG Detector probes
SEQ ID NO:35
  TCATCTGCTGGATG
SEQ ID NO:36
  GATCTGGTCATCCAG
SEQ ID NO:37
  TCATCTGCTGGATGAC
SEQ ID NO:38
  GATCTGGTCATCCAGC
SEQ ID NO:39
  GTCATCCAGCAGATGA
SEQ ID NO:40
  GCTGGATGACCAGATC All pairwise combinations of the upstream and downstream amplification primers with all pairwise combinations of bumper primers were tested in four SDA reaction conditions to identify the best primer combination and to optimize the amplification reaction:

| | KPO$_4$ (mM) | Temp. (°C.) | Glycerol (%) |
|---|---|---|---|
| A | 25 | 50 | 12 |
| B | 25 | 52 | 7 |
| C | 35 | 50 | 7 |
| D | 35 | 52 | 12 |

Strains LCDC 724, TMC 1201, T8594 and T10892 were selected for amplification. The tSDA protocol was essentially as described in EP 0 684 315. All amplification primer pairs produced detectable amplification products in both typical and atypical strains under most of the reaction conditions tested. The most efficient amplification was obtained with SEQ ID NO:23 and SEQ ID NO:28 in reaction D. These amplification primers and reaction conditions were then selected for further study to evaluate all pairwise combinations of left and right bumper primers. In this experiment SEQ ID NO:29 and SEQ ID NO:30 gave the most efficient amplification in both typical and atypical strains, but all bumper combinations functioned efficiently in the reaction. In similar tests, SEQ ID NO:37 was found to be the most effective detector oligonucleotide, although all detector probes gave satisfactory results.

To determine the sensitivity of a tSDA assay using amplification primers SEQ ID NO:23 and SEQ ID NO:28, a genome titration experiment was performed. The isolated genomes of one typical strain (TMC1201) and two atypical strains (T8594 and T10892) of *M. kansasii* were diluted in human placental DNA to obtain initial target levels of $10^4$, $10^3$, $10^2$, 10 and 1 genomes. The tSDA reactions were performed as above using the conditions of reaction D and the most efficient bumpers and detector. A minimum of ten genome copies was detectable by autoradiography for atypical strain T10892 and a minimum of 100 genome copies was detectable for TMC1201 and T8594. The sensitivity of the assay is therefore between 1 and 10 genome copies for T10892 and between 10 and 100 genome copies for the TMC1201 and T8594.

The same optimized set of primers and probes was used in tSDA to further evaluate species-specificity and cross-reactivity. A variety of typical and atypical strains of *M. kansasii* were tested as described above, using pooled templates for cross-reactivity analysis. In the pooled cross-reactivity reactions, $10^7$ genomes of each of five non-*M. kansasii* species were mixed in a single sample for amplification. To identify false negatives due to amplification inhibition in the pooled samples, a control sample which contained the non-*M. kansasii* pool and $2\times10^4$ genome copies of *M. kansasii* TMC1201 was amplified. Four such pools (20 non-*M. kansasii* species) and their related controls were amplified under reaction condition D as described above. The *M. kansasii* strains tested were TMC1201, LCDC711, LCDC714, T1689, T10892, LCDC725, T8494, LCDC724, T1 1792, 5C8246, 4699, 5292, T5993, T686, T7193, T785, T8394, T8794, T8894, T9694, T9194 and T9494. The non-*M. kansasii* species tested were *M. tuberculosis* H37Rv, *M. gordonae* ATCC14470, *M. gastri* LCDC1301, *M. marinum* LCDC801, *M. smegmatis* TMCC1533 (Pool 1); *M. avium* CDC33, *M. intracellulare* 11350, *M. chelonae* TMC1543, *M. simiae* CDC2, *M. xenopi* 1482 (Pool 2); *M. fortuitum* 2808, *M microti* LCDC203, *M. celatum* 51131, *M. scrofulaceum* 19981 and *P. acnes* ATCC6919 (Pool 3); *A. israelii* ATCC10049, *C. diphtheriae* ATCC11913, *N. asteroides* ATCC3308, *R. rhodochrous* ATCC13808 and *S. somaliensis* 33210 (Pool 4). Amplification products were readily detectable for all twenty-two *M. kansasii* strains, with equally strong signals observed in each strain. Each of the pooled samples of non-*M. kansasii* targets was negative for amplification except for the positive controls which also contained *M. kansasii* targets.

The foregoing tests for *M. kansasii* amplification specificity using primers and probes derived from KATS1 or its complement were 100% positive in both PCR and tSDA. Amplification was found to be 100% negative for non-*M. kansasii* species.

As nucleic acids do not require complete complementarity in order to hybridize, it is to be understood that the probe and primer sequences herein disclosed may be modified so as to be substantially identical to the KATS1 sequences disclosed herein without loss of species-specificity and without loss of utility as *M. kansasii*-specific probes and primers. As is known in the art, hybridization of complementary and partially complementary nucleic acid sequences may be accomplished by adjustment of the hybridization conditions to increase or decrease stringency (i.e., adjustment of hybridization temperature or salt content of the buffer). Such minor modifications of the disclosed sequences are equivalents, and any necessary adjustments of hybridization conditions to maintain *M. kansasii*-specificity require only routine experimentation and are within the ordinary skill in the art.

*M. kansasii*-specific amplification products generated using the inventive primers may be detected by a characteristic size, for example on polyacrylamide or agarose gels stained with ethidium bromide. Alternatively, *M. kansasii* nucleic acid in a sample or specifically amplified *M. kansasii* target sequences may be detected by means of an assay probe. Assay probes according to the invention consist of at least about 10 consecutive nucleotides of a KATS1 sequence or the complement thereof. The maximum length of the probe is the length of the particular KATS1 sequence or KATS1 consensus sequence selected. That is, a probe derived from the TMC 1201 KATS1 sequence (SEQ ID NO:4) is about 10–655 nucleotides long, from the LCDC724 KATS1 sequences (SEQ ID NO:3) is about 10–656 nucleotides long, and from the LCDC 724/TMC 1201 consensus sequence (SEQ ID NO:5) is about 10–658 nucleotides long. An assay probe derived from the KATS1 sequences of the other strains described herein and shown in the SEQUENCE LISTING is about 10–605 nucleotides long (SEQ ID NOs: 11, 12, 14, 17 and 18), about 10–604 nucleotides long (SEQ ID NO:15), about 10–602 nucleotides long (SEQ ID NO: 16), about 10–606 nucleotides long (SEQ ID NO: 13), about 10–540 nucleotides long (SEQ ID NO:19), or about 10–558 nucleotides long (SEQ ID NO:20). An assay probe derived from the consensus sequence SEQ ID NO:21 is about 10–661 nucleotides long. All such probes are expected to retain *M. kansasii* specificity, as sequence homology searches were performed for all subsequences consisting of 10 consecutive nucleotides of the KATS1 sequence and no homologies were found. Assay probes derived from any of these sequences are typically about 10–75 consecutive nucleotides in length, preferably about 15–50 consecutive nucleotides.

When amplification products are detected, the assay probe is typically selected to hybridize to a sequence which is between the amplification primers, i.e., it is generally an internal probe. A labeled amplification primer may also be used as an assay probe. In one embodiment, the labeled amplification primer or the labeled internal assay probe is extended on the target sequence (a detector primer) for detection of target sequences as described by Walker, et al., Nucl. Acids Res., supra.

The detectable label of the assay probe is a moiety which can be detected either directly or indirectly as an indication of the presence of the target nucleic acid. For direct detection of the label, assay probes may be tagged with a radioisotope and detected by autoradiography, or tagged with a fluorescent moiety and detected by fluorescence as is known in the art. Alternatively, the assay probes may be indirectly detected by tagging with a label which requires additional reagents to render it detectable. Indirectly detectable labels include, for example, chemilumninescent agents, enzymes which produce visible reaction products and ligands (e.g., haptens, antibodies or antigens) which may be detected by binding to labeled specific binding partners (e.g., antibodies or antigens/haptens). Ligand labels are also useful for solid phase capture of the oligonucleotide (capture probes). Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate, and the chemiluminescent signal is developed and read in a luminometer. As another alternative for detection of amplification products, a signal primer as described in EP 0 678 582 may be included in an amplification reaction. In this embodiment, labeled secondary amplification products are generated during amplification in a target amplification-dependent manner and may be detected as an indication of target amplification by means of the associated label.

For commercial convenience, KATS1 primers or probes for species-specific detection and identification of *M. kansasii* nucleic acids according to the invention may be packaged in the form of a kit. Typically, such a kit contains at least one pair of amplification primers or at least one assay probe according to the invention. Reagents for performing a nucleic acid amplification or hybridization reaction may also be included in the kit, for example, buffers, additional primers or probes, nucleotides, enzymes, etc. The components of the kit are packaged together in a common container, optionally including instructions for performing a selected embodiment of the inventive methods. Components for detection may also optionally be included in the kit, e.g., a second assay probe, and/or reagents or means for performing label detection.

The target binding sequences of the amplification primers confer hybridization specificity on the oligonucleotides and therefore provide the species-specificity to the inventive methods. Other sequences, as required for performance of a selected amplification reaction, may optionally be added to the target binding sequences disclosed herein without altering the species-specificity of the amplification reaction. By way of example, the *M. kansasii*-specific amplification primers of the invention may contain a recognition site for the restriction endonuclease BsoBI which is nicked during the SDA reaction. It will be apparent to one skilled in the art that other nickable restriction endonuclease recognition sites may be substituted for the BsoBI recognition site, including but not limited to those recognition sites disclosed in EP 0 684 315 and U.S. Pat. No. 5,455,166. Preferably, the recognition site is for a thermophilic restriction endonuclease so that the amplification reaction may be performed under the conditions of thermophilic SDA (tSDA). The tail of the SDA amplification primer is also required for amplification, but its sequence is generally not critical. It is important, however, to avoid including the restriction site used for SDA and to avoid sequences which will hybridize either to their own target binding sequence or to other primers. Amplification primers for SDA according to the invention therefore consist of about 10–25 consecutive nucleotides of a KATS1 sequence disclosed herein or the complement thereof (the 3' target binding sequence), a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. For other amplification reactions, amplification primers according to the invention may consist of only a target binding sequence which is about 10–75 consecutive nucleotides of a KATS1 sequence or the complement thereof, preferably about 15–50 consecutive nucleotides (e.g., for PCR or LCR). Amplification primers according to the invention may also consist of a target binding sequence which is about 10–75 consecutive nucleotides of KATS1 or its complement and the additional sequences required for the selected amplification reaction as is known in the art (e.g., a promoter recognized by RNA polymerase for 3SR). For LCR, two or more target binding sequences which are adjacent in KATS1 or its complement, each about 10–75 nucleotides long, are necessary to prepare multiple amplification primers which may be ligated together when hybridized to the KATS1 target sequence.

In most species-specific SDA reactions it is not essential that the bumper primers be species-specific, as their function is to displace the downstream, species-specific amplification primers. It is only required that the bumper primers hybridize to the target upstream from the amplification primers so that when they are extended they will displace the amplification primer and its extension product. The particular sequence of the bumper primer is therefore generally not critical, and may be derived from any upstream target sequence which is sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence. In the present invention, however, the bumpers also comprise at leasat about 10 consecutive nucleotides of a KATS1 sequence or the complement thereof, and therefore all KATS1 bumper primers will also be species-specific. Therefore, all bumper primers derived from KATS1 are also useful as the target binding sequence of an amplification primer or as an assay probe, and vice versa.

Amplification reactions employing the primers of the invention may incorporate thymine as taught by Walker, et al., supra, or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (Ugi) prior to performing the subsequent amplification to prevent excision of dU in newly-formed amplification products.

As all 10 consecutive nucleotide subsequences of KATS1 appear to be unique, any probe which is based on at least about 10 consecutive nucleotides of any of the KATS1 sequences disclosed herein or the complements thereof should also be unique and *M. kansasii*-specific. Similarly, the fact that all 10 nucleotide subsequences of KATS1 appear to be unique allows any subsequence of about 10–75 consecutive nucleotides of any of the KATS1 sequences disclosed herein and their complements, preferably about 15–50 consecutive nucleotides, to be used as a target binding sequence for an *M. kansasii*-specific amplification primer. Further, any adjacent segments of any KATS1 sequence disclosed herein or the complement thereof, each about 10–75 consecutive nucleotides long, may be used as a target binding sequences for ligatable *M. kans

What is claimed is:

1. A method for species-specific detection of *M. kansasii* nucleic acids comprising:

a) hybridizing a probe to the *M. kansasii* nucleic acids, the probe consisting of at least fifteen consecutive nucleotides of sequence, at least any one of SEQ ID NOs:3–5 any one of SEQ ID NOs:11–21 a complement of any one of SEQ ID NOs:3–5 or a complement of any one of SEQ ID NOs: 11–21, and;

b) detecting the *M. kansasii* nucleic acids by detecting probe hybridization.

2. The method of claim 1 wherein the probe is about 15–50 nucleotides long.

3. The method of claim 1 wherein probe hybridization is detected by means of a detectable label.

4. A method for species-specific detection of *M. kansasii* nucleic acids comprising:

a) hybridizing to the *M. kansasii* nucleic acids an amplification primer consisting of a target binding sequence and, optionally, a sequence for amplification of the target nucleic acid, the target binding sequence consisting of at least fifteen consecutive nucleotides of any one of SEQ ID NOs:3–5, any one of SEQ ID NOs: 11–21, a complement of any one of SEQ ID NOs:3–5 or a complement of any one of SEQ ID NOs:11–21;

b) amplifying the *M. kansasii* nucleic acids by extension of the hybridized amplification primer, and;

c) detecting the amplified *M. kansasii* nucleic acids.

5. The method of claim 4 wherein the target binding sequence of the amplification primer is selected from the group consisting of the target binding sequences of SEQ ID NOs:23–28.

6. The method of claim 5 wherein the amplification primer is selected from the group consisting of SEQ ID NOs:23–28.

7. The method of claim 4 wherein the amplified *M. kansasii* nucleic acids are detected by means of an assay probe.

8. The method of claim 7 wherein the assay probe is selected from the group consisting of SEQ ID NOs:35–40.

9. A method for species-specific detection of *M. kansasii* nucleic acids comprising:
   a) hybridizing to the M kansasii nucleic acids a first and a second amplification primer, the first and the second amplification primers each consisting of at least fifteen consecutive nucleotides of any one of SEQ ID NOs:3–5, any one of SEQ ID NOs: 11–21, a complement of any one of SEQ ID NOs:3–5 or a complement of any one of SEQ ID NOs:11–21, wherein the first and second amplification primers are selected such that the first and second amplification primers are adjacent and ligatable when hybridized to the *M. kansasii* nucleic acids;
   b) ligating the hybridized first and second amplification primers to produce an amplification product, and;
   c) detecting the amplification product.

10. The method of claim 9 wherein the amplification product is detected by means of an assay probe.

11. An oligonucleotide consisting of at least fifteen consecutive nucleotides of any one of SEQ ID NOs:3–5 any one of SEQ ID NOs:11–21, a complement of any one of SEQ ID NOs:3–5 or a complement of any one of SEQ ID NOs: 11–21.

12. The oligonucleotide of claim 11 which is about 15–50 nucleotides long.

13. The oligonucleotide of claim 11 selected from the group consisting of the target binding sequences of SEQ ID NOs:23–28, SEQ ID NOs:29–40, and complements thereof.

14. An oligonucleotide consisting of about 15–50 consecutive nucleotides of any one of SEQ ID NOs:3–5, any one of SEQ ID NOs:11–21, a complement of any one of SEQ ID NOs:3–5 or a complement of any one of SEQ ID NOs:11–21 and, optionally, a sequence for amplification of a target nucleic acid.

15. The oligonucleotide of claim 14 selected from the group consisting of SEQ ID NOs:6–10, SEQ ID NO:22, the target binding sequences of SEQ ID NOs:23–38 and SEQ ID NOs:29–40.

16. A kit for species-specific detection of *M. kansasii* nucleic acids comprising:
   a) an oligonucleotide consisting of
      i) at least fifteen consecutive nucleotides of any one of SEQ ID NOs:3–5, any one of SEQ ID NOs:11–21, a complement of any one of SEQ ID NOs:3–5 or a complement of any one of SEQ ID NOs: 11–21, or
      ii) a target binding sequence and, optionally, a sequence for amplification of the nucleic acids, the target binding sequence consisting of at least fifteen consecutive nucleotides of any one of SEQ ID NOs:3–5, any one of SEQ ID NOs:11–21, a complement of any one of SEQ ID NOs:3–5 or a complement of any one of SEQ ID NOs: 11–21, and
   b) means for detecting the *M. kansasii* nucleic acids using the oligonucleotide.

* * * * *